United States Patent [19]

Woo

[11] Patent Number: 4,507,492

[45] Date of Patent: Mar. 26, 1985

[54] PREPARATION OF AROMATIC DERIVATIVES

[75] Inventor: Edmund P. Woo, Midland, Mich.

[73] Assignee: The Dow Chemical Company, Midland, Mich.

[21] Appl. No.: 492,114

[22] Filed: May 6, 1983

[51] Int. Cl.$^3$ .............................................. C07C 41/16
[52] U.S. Cl. ...................................... 560/64; 564/393; 568/27; 568/38; 568/433; 568/640; 568/646; 568/656; 568/657
[58] Field of Search ............... 568/657, 656, 640, 433, 568/646, 27, 38; 564/393; 560/64

[56] References Cited

U.S. PATENT DOCUMENTS 4,192,949  3/1980  Merger et al. ...................... 568/656

FOREIGN PATENT DOCUMENTS 13663  7/1980  European Pat. Off. .

OTHER PUBLICATIONS

Takahashi et al., Bull. Chem. Soc. Japan, vol. 45, (1972), 230–236.
Jeffrey et al., Jour. Org. Chem., vol. 47, (1982), 587–590.
Atkins, *Tet. Lett.*, 43, 3821–3824, (1970).
Jeffrey et al., *J. Org. Chem.*, 47, 587–590, (1982).

*Primary Examiner*—Bernard Helfin
*Attorney, Agent, or Firm*—Douglas N. Deline; Paul M. Bork; Michael S. Jenkins

[57] ABSTRACT

Allyl derivatives of phenols, thiophenols and arylamines are prepared by contacting such aromatic reactant with an allyl lower alkyl carbonate in the presence of a molybdenum, tungsten or Group VIII metal.

20 Claims, No Drawings

PREPARATION OF AROMATIC DERIVATIVES

BACKGROUND OF THE INVENTION

The present invention relates to aromatic derivatives. More particularly the present invention relates to a novel method of preparing allyl derivatives of phenols, thiophenols and arylamines by the reaction of such phenol, thiophenol or arylamine compounds with an allyl lower alkyl carbonate compound.

Previous methods for preparation of allyl ethers of phenolic compounds involves the reaction of the phenolic compound with a stoichiometric amount of base. The process is well-known in the art having been disclosed in U.S. Pat. Nos. 4,060,563 and 3,318,765. Disadvantageously, the prior art process forms large amounts of a salt by-product and at least one paper has found significant amounts of ring allylated reaction products result from the reaction of 2,6-dimethylphenol, allyl bromide and sodium ethoxide in ethanol solution, see, Tarbell et al., *J.A.C.S.*, 62, 728 (1940).

It is previously known to form allylic derivatives of carbon acids by contacting the same with allylic alcohols, amines or esters in the presence of homogeneous palladium catalysts. See, K. E. Atkins, *Tet. Lett.*, 43, 3821–3824 (1970). The process has been found suitable only for strongly acid compounds such as acetylacetone.

In my previously filed patent application, U.S. Pat. No. 4,362,670, I have taught a process for allylating carbon acid compounds by contacting the carbon acid with an allyl carbonate in the presence of a palladium catalyst.

In EP 13,663, the procedure for deprotecting allyl-substituted esters or other oxycarbonyl functional compounds employing organic-soluble palladium complexes is disclosed. In Example 8, N-octadecyl allyl carbonate was reacted with ethylhexanoic acid resulting in the preparation of n-octadecanol. The work is additionally described in a paper by the inventors, P. D. Jeffrey et al., *J. Org. Chem.*, 47, 587–590 (1982).

K. Takahashi et al., *Bull. Soc. Japan*, 45, 230–236 (1972), disclosed that allylic ethers and esters reacted with phenols, alcohols, carboxylic acids, primary and secondary amines and active methylene compounds in the presence of a zero valent palladium phosphine complex.

Illuminati et al. in U.S. Pat. No. 4,182,726, taught the reaction of phenols or acyl ester derivatives thereof with dialkyl carbonates and arylalkyl carbonates in the presence of various Lewis acid catalysts.

SUMMARY OF THE INVENTION

According to the present invention there is provided an improved process for the preparation of an allyl derivative of an aromatic compound corresponding to the formula:

$$Ar\text{-}(XCR_1R_2CR_3=CR_4R_5)_n$$

wherein:
Ar is an aromatic radical of valence n optionally further substituted with one or more unreactive substituents, R;
X is —O—, —S— or —NR$_6$—;
R$_1$, R$_2$, R$_3$, R$_4$, R$_5$ and R$_6$ independently each occurrence are hydrogen or a C$_{1-20}$ hydrocarbyl group optionally further substituted with one or more unreactive substituents, R; and
n is an integer greater than zero,
comprising contacting a phenolic, thiophenolic or arylamine compound corresponding to the formula:

$$Ar(XH)_n$$

wherein Ar, X and n are as previously defined, with an allyl lower alkyl carbonate corresponding to the formula:

$$CR_4R_5=CR_3-CR_1R_2-OC(O)OR_7$$

wherein R$_1$-R$_5$ are as previously defined, and R$_7$ is lower alkyl in the presence of a catalytic amount of a catalyst comprising a metal selected from the group consisting of molybdenum, tungsten and the metals of group VIII.

DETAILED DESCRIPTION OF THE INVENTION

The phenolic, thiophenolic and arylamine compounds for use according to the present invention are any aromatic compound containing at least one ring-substituting hydroxyl, thiol or amine moiety. Included are both monomeric and polymeric compounds containing one or more reactive —XH moieties. The aromatic radical, Ar, of valence n may be further illustrated by the following non-limiting examples;

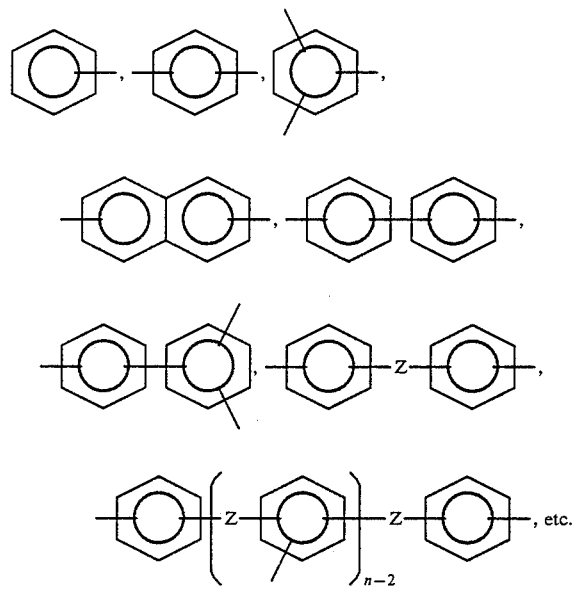

where Z is —O—, —S— or C$_{1-4}$ alkylene.

By the term "unreactive substituents" are meant ring substituents that are unreactive and non-interfering with the desired reaction of the present invented process. The unreactive substituents, R, may be further illustrated by the following non-limiting embodiments. Suitably R is selected from the group consisting of halo, nitro, C$_{1-20}$ hydrocarbyl, C$_{1-20}$ hydrocarboxy, C$_{1-20}$ hydrocarbylthio, C$_{1-20}$ hydrocarboxycarbonyl, C$_{1-20}$ hydrocarbylsulfinyl, C$_{1-20}$ hydrocarbonyl and formyl. By the term halo are included fluoro, chloro, bromo and iodo substituents. By the term hydrocarbyl are included alkyl, aryl, alkenyl, alkadienyl, alkaryl, aralkyl, alkenylaryl, aralkenyl, etc., groups. By the term hydrocarboxy are included alkoxy, alkenoxy, alkyl(poly)oxyalkylene, alkoxy(poly)alkyleneoxy, aryloxy, aroxyaryl, alkoxyaryl, alkenoxyaryl, alkenoxyalkyl, etc., groups. By the term hydrocarbylthio are included the corresponding sulfur-containing analogs of the previously mentioned hydrocarboxy groups. By the term hydrocarboxycarbonyl are included substituents of the formula —C(O)OR$_8$ wherein R$_8$ is alkyl, alkenyl, aryl, alkaryl, or halo-, nitro- or alkoxy-substituted derivatives thereof. By the term hydrocarbylsulfinyl are included substituents of the formula —S(O)R$_8$ wherein R$_8$ is as previously defined. By the term hydrocarbonyl are included substituents of the formula —C(O)R$_8$ wherein R$_8$ is as previously defined.

Preferred substituents, R, include halo, especially chloro or bromo; hydrocarbyl, especially $C_{1-4}$ alkyl or phenyl; formyl; hydrocarbonyl, especially acetyl; and hydrocarbyloxy, especially $C_{1-4}$ alkoxy.

Preferred aromatic reactants are the phenolic compounds particularly mono- and bicyclic phenolic compounds such as the phenols and bisphenols. A most particularly preferred aromatic reactant is bisphenol A.

The allyl lower alkyl carbonates for use according to the present invention are known compounds or else they may be prepared by techniques previously known in the art. Preferred allyl lower alkyl carbonate are those wherein $R_1$–$R_5$ are hydrogen or methyl and $R_7$ is methyl or ethyl. Most preferably $R_1$–$R_5$ are hydrogen and $R_7$ is methyl, e.g., allyl methyl carbonate. One preferred method of preparation of the allyl lower alkyl carbonate is to prepare an equilibrium mixture of the compound in situ, for example, by a transcarbonation reaction between an allylic alcohol and a dilower alkyl carbonate in the presence of base.

Use of an allyl lower alkyl carbonate in the manufacture of the aromatic derivatives of the present invention is particularly desirable because the corresponding reaction by-product is a lower alkanol. Separation of the reaction by-products from the desired aromatic derivatives can thereafter be performed by a simple distillation at relatively mild temperatures. Because the aromatic products of the invention are susceptible to a Claisen rearrangement at elevated temperatures resulting in ring-substituted ortho-allylated reaction by-products, it is a particularly advantageous feature of the present invented process that the lower alkanol by-product is readily separated from the desired aromatic product at relatively mild temperatures so as to avoid substantial formation of the above-described rearrangement products.

The catalysts for use according to the present invention are preferably complexes of the molybdenum, tungsten or group VIII metal and may be either homogeneous or heterogeneous. Representative are the phosphine, phosphite, arsine or stibine complexes of such metals as well as complexes formed from polymeric ligands such as functionalized styrene divinylbenzene copolymers containing functional groups that are capable of forming complexes with molybdenum, tungsten or group VIII metals.

The catalysts may be prepared from homogeneous sources of the metal such as metal organyl compounds or metal halides, nitrates, etc. Reducing agents such as sodium borohydride, etc., to prepare the zero valent state of the metal may be employed if desired.

It has also been found that heterogeneous sources of the metal may also be employed in the process. The metal or even an oxide thereof such as commonly available supported metal catalysts in the presence of phosphine, phosphite, arsine or stibine ligands are also effective catalysts for the process. Suitable supports include carbon, diatomaceous earth, silica, alumina, zeolites, etc. Preferred is carbon. Repeated reactions using such catalyst systems without loss of activity indicate that the metal is apparently not irreversibly leached from the supported noble metal source.

Preferred metals are palladium, platinum and nickel. Most preferred is palladium. Preferably, the catalyst is the corresponding triorganyl phosphine complex of a zero valent metal, e.g., trialkyl or triaryl phosphine complexes. The amount of complex-forming ligand employed is from about 0.5 to 4 equivalents per equivalent of metal based on the stoichiometry of the complex formed.

According to the invention, the allyl lower alkyl carbonate, aromatic reactant and catalytic amount of the metal catalyst are contacted under an inert atmosphere until the evolution of carbon dioxide ceases. The product may then be recovered by distillation. By-product, lower alkanol, may be stripped from the reaction mixture during the course of the reaction where suitably elevated reaction temperatures are employed or distilled after the reaction is complete.

As previously mentioned, the reaction is conducted at a temperature so as to avoid formation of substantial amounts of C-allylated reaction products. Suitably, the reaction is conducted at a temperature from about −20° C. to about 150° C. Preferred temperatures are from about 20° C. to about 100° C. Most preferred is a temperature from about 35° C. to about 80° C. Reduced or elevated temperatures may be employed if desired. Preferred pressures are atmospheric. Reaction vessels of ordinary design and construction may be employed. Suitable are ordinary glass or glass-lined vessels. Reaction times from 0.1 hour to about 100 hours may be required, depending on the reactants and reaction conditions employed.

The presence of a solvent is not essential to the reaction but a solvent may be employed if desired to aid in temperature control and in the efficient mixing and contacting of reactants. Ethereal solvents, such as alkyl ethers, (poly)oxyalkylene ethers and tetrahydrofuran may be used. Other suitable solvents include aromatic hydrocarbons, ketones, esters, cyanoalkanes, alkanols and chlorinated hydrocarbons.

The amount of catalyst employed based on weight of metal and allyl lower alkyl carbonate is from about 0.01 to about 10 percent and preferably from about 0.1 to about 2 percent.

SPECIFIC EMBODIMENTS

Having described my invention, the following examples are provided as further illustrative and are not to be construed as limiting. Yields are based on aromatic reactant.

Example 1: Diallyl ether of bisphenol A

A mixture of bisphenol A (114 g, 0.5 mole), allyl methyl carbonate (140 g, 1.20 moles), 5 percent palladium on charcoal (1.0 g, 0.00047 mole of palladium) and triphenyl phosphine (0.25 g, 0.00094 mole) is heated at reflux until the evolution of carbon dioxide ceases (3.5 hours). The mixture is filtered to remove the catalyst and decolorized with charcoal to give 152 g, 98.7 percent of the diallyl ether of bisphenol A. The product's structure and the absence of C-alkylation product(s) are confirmed by nuclear magnetic resonance analysis.

Example 2: p-Allyloxybenzaldehyde

A mixture of p-hydroxybenzaldehyde (4.0 g, 33 mmoles), allyl methyl carbonate (16.0 g, 138 mmoles), 5 percent palladium on charcoal (1.3 g, 0.6 mmole palladium) and triphenyl phosphine (0.086 g, 0.32 mmole) is refluxed overnight. After removal of the catalyst and distillation (90° C., 0.6 mm Hg), 4.54 g, 85 percent of substantially pure p-allyloxybenzaldehyde is obtained.

Example 3: Allyl 4-chlorophenyl ether

A mixture of 4-chlorophenol (1.28 g, 10 mmoles), allyl methyl carbonate (1.40 g, 12 mmoles), palladium acetate (11 mg, 0.05 mmole) and triphenyl phosphine (40 mg, 0.15 mmole) is heated at 70° C. for 2.5 hours. After removal of volatiles, the residue is subjected to bulb-to-bulb distillation (110° C., 4 mm Hg) to give 1.64 g, 97 percent of allyl 4-chlorophenyl ether.

Example 4: Allyl 2,6-dimethylphenyl ether

A mixture of 2,6-dimethylphenol (1.22 g, 10 mmoles), allyl methyl carbonate (1.40 g, 12 mmoles), 5 percent palladium on charcoal (26 mg, 0.0125 mmole paladium) and triphenyl phosphine (20 mg, 0.0375 mmole) is heated at 70° C. for 45 minutes. Filtration of the catalyst and bulb-to-bulb distillation of the residue at 120° C., 10 mm Hg gives 1.60 g of substantially pure allyl 2,6-dimethylphenyl ether, 98.7 percent yield.

Examples 5-7

The reaction conditions of Example 4 are substantially repeated employing allyl methyl carbonate (approximately 10 mmoles), 5 percent palladium on charcoal (about 10 mole percent Pd based on carbonate reactant), triphenyl phosphine (about 0.04 mmole) and about 10 mmoles of the aromatic reactants further identified in Table I. Reaction times, products recovered and yields are contained in Table I.

Example 8

The reaction conditions of Example 4 are again substantially repeated excepting that the carbonate reactant is 1-(2-butenyl)methyl carbonate (approximately 10 mmoles) and the aromatic reactant is p-t-butylphenol. After about 4 hours, the reaction is stopped and the product recovered. Analysis by nuclear magnetic resonance spectra indicates a product mixture of 73 percent by weight 3-(1-butenyl)4-t-butylphenyl ether and 27 percent by weight 1-(2-butenyl)4-t-butylphenyl ether are formed. Overall yield is 95 percent based on aromatic reactant.

Example 9: Poly(allylether) of poly(para-vinylphenol)

Allyl alcohol (128.6 g, 2.22 moles), dimethyl carbonate (199.6 g, 2.22 moles) and sodium methoxide catalyst (0.30 g) are added to a reactor and maintained at room temperature (25° C.) with stirring under a nitrogen atmosphere. An equilibrium mixture of allylmethyl carbonate, diallyl carbonate and methanol is rapidly formed. After 30 minutes poly(para-vinylphenol) (26.77 g, 0.00765 mole), triphenyl phosphine (0.06 g) and 5.0 percent palladium on carbon (0.24 g) are added to the reactor and heating is started. The poly(para-vinylphenol) used is a commercial grade product with a 3500 average molecular weight that is dried before use. The reaction mixture is maintained for 4 hours at 82° C. and then cooled to 40° C. Filtration through Celite, followed by vacuum stripping at 100° C. and 10 mm provides a light amber-colored, tacky solid (34.2 g, 95.2 percent yield). Nuclear magnetic resonance spectroscopy confirms the product as the poly(allylether) of poly(para-vinylphenol), wherein approximately 100 percent of the phenolic hydroxyl groups are converted to allylether groups.

Example 10: Poly(allylether) of brominated poly(para-vinylphenol)

Allyl alcohol (144.2 g, 2.48 moles), dimethyl carbonate (223.6 g, 2.48 moles) and sodium methoxide catalyst (0.33 g) are added to a reactor and maintained at room temperature (25° C.) with stirring under a nitrogen atmosphere. An equilibrium mixture of allylmethyl carbonate, diallyl carbonate and methanol is rapidly formed. After 30 minutes brominated poly(para-vinylphenol) (50.0 g, 0.0050 mole), triphenyl phosphine (0.06 g) and 5.0 percent palladium on carbon (0.25 g) are added to the reactor and heating is commenced. The brominated poly(para-vinylphenol) used is a commercial grade product with a 10,000 average molecular weight containing an average of 1.03 bromine atoms per para-vinylphenol unit. The reaction mixture is maintained for 6 hours at 82° C. and then cooled to 25° C. Filtration through Celite, followed by vacuum stripping at 100° C. and 10 mm provides a light tan-colored solid (58.5 g, 99.2 percent yield). Nuclear magnetic resonance spectroscopy confirms the product is the poly(allylether) of brominated poly(para-vinylphenol), wherein 88 percent of the phenolic hydroxyl groups are converted to allylether groups.

The allyl derivatives prepared by the present process are extremely useful as cross-linking agents in polymer

TABLE I

| Run | Aromatic Reactant | Reaction Time (hr) | Product | % Yield |
|---|---|---|---|---|
| 5 | H3C—(ring with CH3, CH3)—OH | 3 | H3C—(ring with CH3, CH3)—OCH2CH=CH2 | 96.0 |
| 6 | H3COC(O)—(ring)—OH | 2 | H3COC(O)—(ring)—OCH2CH=CH2 | 91.0 |
| 7 | phenol | 1 | phenyl allyl ether | 98.5 | systems containing ethylenic unsaturation. In addition, the di- and polyallyl derivatives are self-polymerizable producing resins of high strength and impact resistance for molding and casting applications.

What is claimed is:

1. A process for preparing an allyl derivative of an aromatic compound corresponding to the formula:

$$Ar(XCR_1R_2CR_3=CR_4R_5)_n$$

wherein:

Ar is an aromatic radical of valence n optionally further substituted with one or more unreactive substituents, R;

X is —O—, —S— or —NR$_6$—;

R$_1$, R$_2$, R$_3$, R$_4$, R$_5$ and R$_6$ independently each occurrence are hydrogen or a C$_{1-20}$ hydrocarbyl group optionally further substituted with one or more unreactive substituents, R, wherein R is as previously defined; and n is an integer greater than zero, comprising contacting a phenolic, thiophenolic or arylamine compound corresponding to the formula:

$$Ar(XH)_n$$

wherein Ar, X and n are as previously defined, with an allyl lower alkyl carbonate corresponding to the formula:

$$CR_4R_5=CR_3-CR_1R_2-OC(O)OR_7$$

wherein R$_1$-R$_5$ are as previously defined, and R$_7$ is lower alkyl in the presence of a catalytic amount of a catalyst comprising a metal selected from the group consisting of molybdenum, tungsten and group VIII metals.

2. A process according to claim 1 wherein in the allyl lower alkyl carbonate R$_1$-R$_5$ are hydrogen or methyl and R$_7$ is methyl or ethyl.

3. A process according to claim 2 wherein the allyl lower alkyl carbonate is allyl methyl carbonate.

4. A process according to claim 1 wherein R is selected from the group consisting of halo, nitro, C$_{1-20}$ hydrocarbyl, C$_{1-20}$ hydrocarboxy, C$_{1-20}$ hydrocarbylthio, C$_{1-20}$ hydrocarboxycarbonyl, C$_{1-20}$ hydrocarbylsulfinyl, C$_{1-20}$ hydrocarbonyl and formyl.

5. A process according to claim 4 wherein R is selected from the group consisting of halo, hydrocarbyl, hydrocarbonyl, hydrocarboxy and formyl.

6. A process according to claim 5 wherein R is selected from the group consisting of chloro, bromo, C$_{1-4}$ alkyl, phenyl, acetyl and C$_{1-4}$ alkoxy.

7. A process according to claim 1 wherein X is —O—.

8. A process according to claim 7 wherein the aromatic compound is a phenol or bisphenol compound.

9. A process according to claim 8 wherein the aromatic compound is bisphenol A.

10. A process according to claim 7 wherein the aromatic compound is poly(para-vinylphenol) or brominated poly(para-vinylphenol).

11. A process according to claim 1 wherein the catalyst is a complex of the metal and a phosphine, phosphite, arsine, stibine or complex foaming polymer ligand.

12. A process according to claim 11 wherein the metal is a metal organyl, halide or nitrate.

13. A process according to claim 11 wherein the metal catalyst comprises a supported metal.

14. A process according to claim 11 wherein the metal is palladium, platinum or nickel.

15. A process according to claim 14 wherein the metal is palladium.

16. A process according to claim 11 wherein the catalyst comprises a triorganyl phosphine complex of the zero valent metal.

17. A process according to claim 1 wherein the temperature is selected so as to substantially avoid the formation of ring-substituted allylated reaction by-products.

18. A process according to claim 17 wherein the temperature is from about −20° C. to about 150° C.

19. A process according to claim 18 wherein the temperature is from about 20° C. to about 100° C.

20. A process according to claim 19 wherein the temperature is from about 35° C. to about 80° C.

UNITED STATES PATENT AND TRADEMARK OFFICE
CERTIFICATE OF CORRECTION

PATENT NO. : 4,507,492

DATED : March 26, 1985

INVENTOR(S) : Edmund P. Woo

It is certified that error appears in the above-identified patent and that said Letters Patent is hereby corrected as shown below:

Column 2, line 29, the word "examples;" should be followed by a colon, as in -- examples: --.

Column 3, line 27, the word "carbonate" should be plural, as in -- carbonates --.

Column 5, line 25, the word "paladium" should be spelled -- palladium --.

Column 7, line 30, the formula shown should read
-- $CR_4R_5=CR_3-CR_1R_2-OC(O)OR_7$ --.

Signed and Sealed this

Third Day of September 1985

[SEAL]

Attest:

DONALD J. QUIGG

Attesting Officer     Acting Commissioner of Patents and Trademarks - Designate